United States Patent [19]

McIntosh

[11] Patent Number: 5,693,072
[45] Date of Patent: *Dec. 2, 1997

[54] BLUNT TIP SURGICAL NEEDLE

[76] Inventor: Charles L. McIntosh, 10500 Greenacres Dr., Silver Spring, Md. 20903

[*] Notice: The term of this patent shall not extend beyond the expiration date of Pat. No. 5,123,910.

[21] Appl. No.: 448,045

[22] Filed: May 23, 1995

Related U.S. Application Data

[63] Continuation of Ser. No. 868,291, Apr. 14, 1992, which is a continuation of Ser. No. 610,387, Nov. 7, 1990, Pat. No. 5,123,910.

[51] Int. Cl.$^6$ .................................................. A61B 17/04
[52] U.S. Cl. ............................................ 606/223; 606/222
[58] Field of Search .................................. 606/222–224; D3/28

[56] References Cited

U.S. PATENT DOCUMENTS

| | | |
|---|---|---|
| 508,745 | 11/1893 | Paul . |
| 837,880 | 12/1906 | Playfoot . |
| 2,008,251 | 7/1935 | Hillenbrand . |
| 2,081,209 | 5/1937 | Wilhelm et al. . |
| 2,708,060 | 5/1955 | Keeton . |
| 2,763,410 | 9/1956 | Walker . |
| 2,786,619 | 3/1957 | Marion . |
| 3,094,123 | 6/1963 | Kurtz . |
| 3,613,684 | 10/1971 | Sheridan ............... 128/347 |
| 3,636,955 | 1/1972 | Kurtz . |
| 3,789,852 | 2/1974 | Kim et al. ............... 128/347 |
| 4,120,255 | 10/1978 | McLain . |
| 4,133,339 | 1/1979 | Naslund . |
| 4,237,892 | 12/1980 | Ritter et al. . |
| 4,392,495 | 7/1983 | Bayers . |
| 4,527,564 | 7/1985 | Eguchi et al. . |
| 4,541,427 | 9/1985 | Koss ....................... 128/305.3 |
| 4,553,410 | 11/1985 | Okada . |
| 4,607,505 | 8/1986 | Dunker et al. . |
| 4,685,904 | 8/1987 | Krebs . |
| 4,710,180 | 12/1987 | Johnson . |
| 4,721,506 | 1/1988 | Teves . |
| 4,790,830 | 12/1988 | Hamacher . |
| 4,808,170 | 2/1989 | Thornton et al. . |
| 4,828,547 | 5/1989 | Sahi et al. . |
| 4,883,469 | 11/1989 | Glazier . |
| 4,883,471 | 11/1989 | Braginetz . |
| 4,901,717 | 2/1990 | Moore . |
| 4,966,143 | 10/1990 | Meinershagen . |

FOREIGN PATENT DOCUMENTS

| | | |
|---|---|---|
| 2657247 | 7/1991 | France . |
| 590192 | 12/1933 | Germany . |

(List continued on next page.)

OTHER PUBLICATIONS

Surgical Atlas & Suture Selection Guide, Davis & Geck, 1988.
The Surgeon's Library, Surgery, Gynecology & Obstetrics, vol. 149, Jul. 1979, "Considerations in the Choice of Surgical Needles," William C. Trier, M.D.

(List continued on next page.)

Primary Examiner—Michael Buiz
Assistant Examiner—Mark S. Leonardo
Attorney, Agent, or Firm—Woodard, Emhardt, Naughton, Moriarty & McNett

[57] ABSTRACT

A surgical needle for use in suturing non-cutaneous soft tissues of the body. The surgical needle includes a needle shaft and a needle tip formed of a rigid material suitable for use inside the body. The needle tip has a body portion integrally formed with and extending from the needle shaft and is tapered along its length. The needle tip is further provided with a blunt head which together with the body portion defines a continuously smooth outer surface lacking any sharp cutting edges. The blunt head is adapted to penetrate muscle and fascia, muscle alone, adipose, pericostal tissue and other non-cutaneous soft tissues or the body while at the same time preventing skin penetration of the gloved hand of an operator.

16 Claims, 5 Drawing Sheets

FOREIGN PATENT DOCUMENTS

| | | |
|---|---|---|
| 1091280 | 10/1960 | Germany . |
| 215233 | 11/1984 | Germany . |
| 205105 | 10/1924 | United Kingdom . |
| WO-A 9001349 | 1/1990 | WIPO . |
| WO-A 8202729 | 8/1993 | WIPO . |

OTHER PUBLICATIONS

Undated "Ethiguard Sutures," Sales Brochure.

*AJR:152*, Jan. 1989 article entitled,The Blunt Needle: A New Percutaneous Access Device, by E. William Atkins, Irvin F. Hawkins, Jr., Christopher Mladinich, Richard Tupler, Roy J. Siragusa and Richard Pry.

*Journal of Obstetrics and Gynaecology* article entitled "The incidence of glove puncture dring caesarean section," by J.R. Smith and J.M. Grant, Apr. 1990.

*Congress Book of Abstracts* Silver Jubilee British Congress of Obstetrics and Gynaecology, London 4–7 Jul. 1989.

Article entitled "Reduction of Glove Puncture" in Surgery, J. Richard Smith, MRCOG, Undated (1990?).

V International Conference on Aids, "The Scientific and Social Challenge" in Montreal, Quebec, Canada, Jun. 4–9, 1989.

BLUNT TIP SURGICAL NEEDLE

This application is a continuation of application Ser. No. 07/868,291, filed Apr. 14, 1992, pending, which is a continuation of Ser. No. 07/610,387 filed Nov. 7, 1990, U.S. Pat. No. 5,123,910 issued Jun. 23, 1992.

BACKGROUND OF THE INVENTION

1. Field of the Invention

The present invention relates generally to the field of surgical instruments and, more specifically, to surgical needles for suturing wounds.

2. Description of the Art

In recent years, there has been an increasing awareness of the problems associated with accidental sticking of medical personnel with suturing and syringe needles. Before the advent of biological warfare contaminants and the spreading of infectious health hazards such as hepatitis B (HBV), human immunodeficiency virus (HIV) infection and acquired immune deficiency syndrome (AIDS), the consequences of sustaining a needle stick wound were not considered serious. However, the knowledge that infectious diseases such as the AIDS virus can be spread by an accidentally inflicted needle-stick from a contaminated needle administered to a person having the AIDS virus has done much to change this belief. Accordingly, there has been an increasing amount of activity in the area of addressing this problem. For example, U.S. Pat. No. 4,828,547 to Sahi et al. describes a needle assembly containing a blunting member which is movable, either by fluid flow through the needle or by mechanical pressure, from a retracted position in which the blunting member does not interfere with the puncture tip of the needle, to an extended position attained after use in which the blunting member extends beyond the punture tip and thereby blunts the needle. Further examples of shield or guard type assemblies for syringe needles are disclosed in U.S. Pat. Nos. 4,883,469 to Glazier and 4,883,471 to Braginetz et al.

While the devices disclosed in the above patents and other similar type devices may be useful for hypodermic syringe needles which are intended to be disposed of after a single "stick", it is not a practicable solution for use with surgical needles since such needles must make repeated "sticks" into the body. While surgeons are highly trained and skilled individuals, the possibility of an accidental stick from a surgical needle is still present. Even a highly skilled surgeon can eventually become tired or, as in trauma situations, in a hurry at the end of a long operation and thus more prone to such an occurrence. Then too, it is not uncommon that a less experienced individual in the operating room team is assigned to close the wound.

The present invention is intended to decrease the potential transmission of all infectious agents, including those referred to above, in situations where accidental needle stick is the means for such transmission.

SUMMARY OF THE INVENTION

The present invention is a surgical needle for use in suturing non-cutaneous soft tissues of the body. In a preferred embodiment thereof, the present invention comprises a needle shaft and a needle tip formed of a rigid material suitable for use inside the body. The needle tip has a body portion integrally formed with and extending from the needle shaft. The body portion is tapered along the length thereof. The needle tip is further provided with a blunt head adapted to penetrate muscle and fascia, muscle alone, adipose, pericostal tissue and other non-cutaneous soft tissues of the body while at the same time decreasing potential skin penetration of the gloved hand of an operator and operating personnel such as surgeons, surgeon assistants, scrub and circulating nurses, fabric care and housekeeping personnel.

As additional features, the blunt head may have a part spherical shape and a vertex which forms a portion of the part spherical shape. Further, the blunt head may have a diameter of curvature which is in a range from about 25% to 62% of the diameter of the needle shaft and the needle tip may be formed so as to have a continuously smooth outer surface lacking any sharp cutting edges.

Accordingly, it is an object of the present invention to provide an improved surgical needle for use in suturing muscle and fascia, muscle alone, adipose, pericostal tissue and other non-cutaneous soft tissues of the body while at the same time significantly decreasing the probability of skin penetration of the gloved hand of an operator.

Related objects and advantages of the present invention will become more apparent by reference to the following figures and detailed description.

DESCRIPTION OF THE PREFERRED EMBODIMENT

Figure 1:
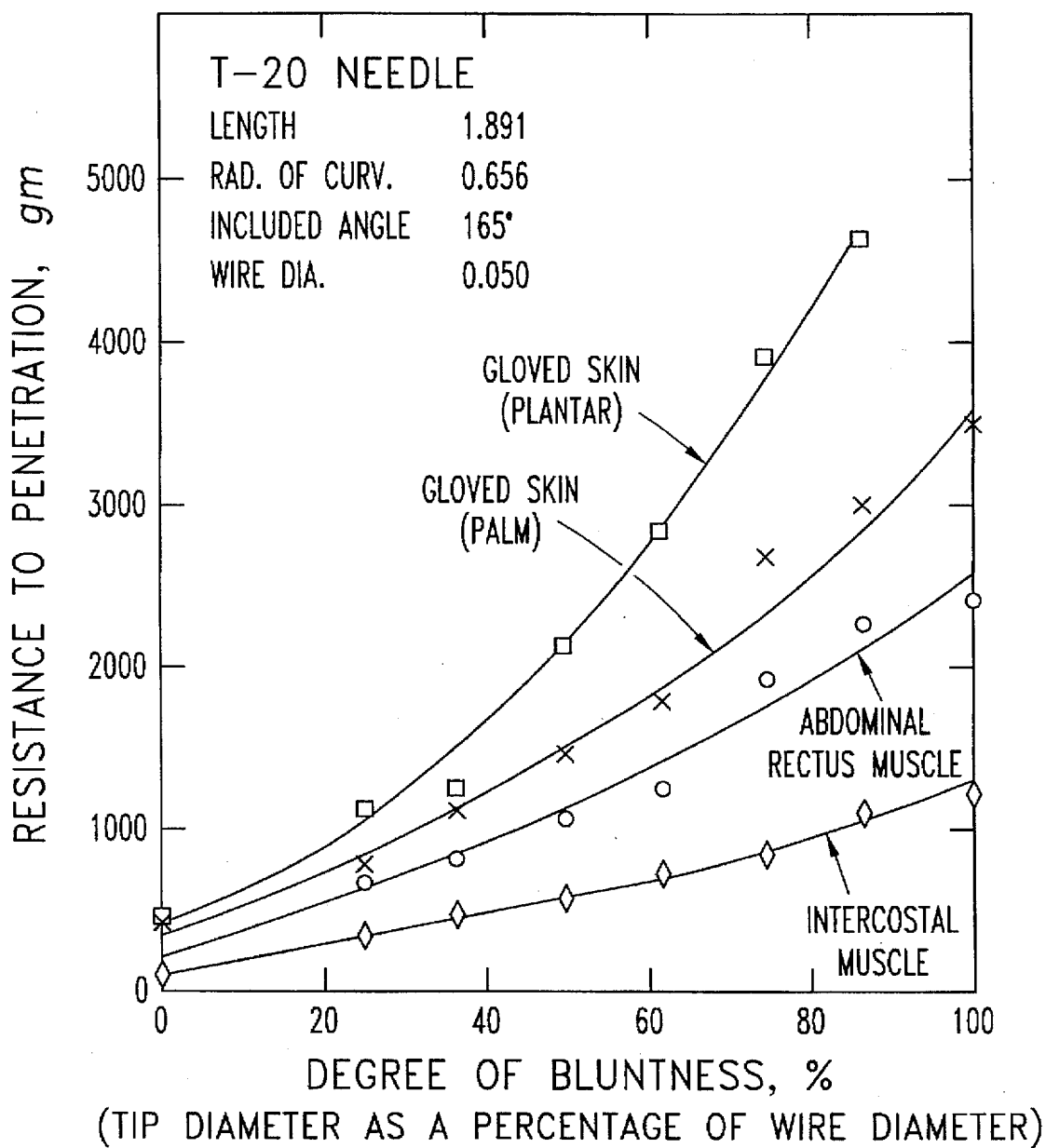
FIG. 1 is a graph showing the relationship between penetration force and needle bluntness using data obtained from Table I.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As used herein, the term "bluntness" is intended to refer to the relation between the diameter of curvature of the needle point or vertex to the diameter of the needle shaft. For comparison purposes, this relationship is expressed as a percentage. As an example, a needle having 50% bluntness is intended to describe a needle having a diameter of curvature at the vertex which is half the diameter of the needle shaft. The term "diameter of curvature" as used herein describes the hypothetical diameter of a fury spherical surface coincident with the part spherical surface which forms the vertex, or forwardmost point, of the needle. Thus, a totally sharp needle, i.e., a needle having 0% bluntness, has zero curvature present at the needle vertex.

A number of tests were conducted to determine whether there existed a blunt needle point configuration which would permit relatively easy penetration of soft non-cutaneous body tissues while providing increased protection against an unintended stick of the gloved hand of the operator. These included tests to determine the penetration force as a function of "bluntness" in muscle/fascia and in gloved palmar skin.

In a first series of tests, four groups of test results were obtained corresponding to the following four test specimens: (1) abdominal rectus muscle/fascia, (2) gloved palmar skin, (3) abdominal rectus muscle/fascia vs. gloved plantar skin, and (4) intercostal muscle. In each group of tests, eight needle point configurations were tested having a bluntness of 0%, 25%, 37%, 50%, 62%, 75%, 87%, and 100%. A sample set of six needles per each configuration were used for each of the first, second and fourth groups of tests, making a total of 48 needles for each of these groups of tests. In the third group of tests, a sample set of twelve needles was used for each needle configuration, making a total of 96 needles for this test group. All needles were type T-20 surgical needles manufactured by the Medical Divice Division of American Cyanamid Company of Danbury, Conn. having a length of 1.891 inches, a wire diameter of 0.050 inches, and a curved shape having a radius of curvature along the needle shaft of 0.656 inches and an included angle of 165 degrees.

The first group of test remits for the abdominal rectus muscle/fascia was conducted as follows. The skin overlying the abdominal fascia of a single cadaver was opened and retracted. The supra-umbilical abdominal rectus muscle with its anterior and posterior sheaths was then excised from the cadaver. Using this specimen, the force of penetration was measured for each of the needles in the sample. A total of three passes were made for each needle. In each pass, penetration was made away from the midline of the specimen so that the penetration sequence would always be fascia, muscle, then fascia.

In the second group of tests, skin from the palms of the same cadaver used in the first series of tests was harvested. The area harvested was bounded proximally by the skin crease at the wrist and distally by the base of the digits. A standard latex procedure glove was placed over the skin specimen in order to simulate unintended puncture of the surgeon's hand. The penetration sequence was glove, epidermis, dermis, and lastly, the back side of the latex glove. As with the first group of tests, the force of penetration was measured for each of the needles in the sample, with a total of three passes being made for each needle.

The goal in the third group of tests was to directly compare the penetration force of gloved skin as compared to that of abdominal rectus muscle/fascia using the same needle. Since all usable palmar skin had been harvested from the test cadaver in performing the previous group of tests and another suitable cadaver was unavailable, plantar skin was harvested from the test cadaver's feet. This skin is similar to the skin of the palm in that both are thick skin areas. Only the central non-weight bearing portion of the plantar skin was used. The rectus muscle and fascia was harvested from the same test cadaver from the umbilicus to just superior to the pubic bone. The rectus muscle/fascia tissue was penetrated first, followed by the gloved plantar skin. In order to assess the difference in penetration force of palmar skin versus plantar skin, several passes were made through some remaining palmar skin after the plantar skin had been penetrated. The results obtained indicated that the penetration force was approximately the same for the two skin specimens using the sharp (0% bluntness) needles, with the plantar penetration force increasing as the bluntness fo the needle increased (approximately twice the penetration force was necessary with a 62% dull needle). Again, the force of penetration was measured for each of the needles in the sample. In this group of tests, one pass was made into both specimens with each needle.

For the fourth group of tests, intercostal muscle was harvested from the same cadaver front interspaces 3 through 5 at the mid-clavicular line. The specimen blocks also consisted of the pleural lining of the chest (parietal pleura). The force of penetration was measured for each of the needles in the sample, with a total of three passes being made for each needle.

Table 1 lists the results of each of the four groups of test results in this first series of tests. Each needle is identified in the table by the letter "D" prefixed by a number indicating the testing order. The penetration force is expressed in grams.

TABLE I

| Group 1 results (Abdominal Rectus Fascia/Muscle): | | | |
| --- | --- | --- | --- |
| 0% | 25% | 37% | 50% |
| 4D 80, 120, 8.0 | 3D 360, 680, 600 | 6D 880, 600, 600 | 5D 920, 960, 1080 |
| 7D 120, 120, 120 | 13D 840, 760, 1000 | 9D 920, 1120, 1000 | 11D 1560, 1000, 1080 |
| 19D 40, 80, 120 | 14D 640, 600, 600 | 12D 720, 840, 880 | 25D 1040, 1160, 920 |
| 30D 80, 120, 80 | 20D 600, 520, 680 | 26D 1160, 760, 720 | 28D 1800, 1000, 1240 |
| 38D 80, 80, 80 | 31D 680, 720, 800 | 27D 520, 840, 840 | 32D 720, 1120, 600 |
| 40D 40, 80, 120 | 36D 840, 640, 840 | 41D 800, 600, 920 | 42D 920, 1400, 1360 |
| 62% | 75% | 87% | 100% |
| 2D 640, 720, 600 | 8D 2520, 2440, 1520 | 15D 2680, 2280, 2560 | 1D 2920, 1200, 2040 |
| 10D 2040, 1200, 1600 | 17D 1200, 1880, 1600 | 21D 1760, 1960, 2120 | 16D 2400, 2760, 3080 |
| 18D 1800, 1720, 1520 | 22D 2440, 1320, 1520 | 34D 2480, 2160, 1800 | 23D 1920, 1680, 2160 |
| 24D 1240, 1520, 1080 | 33D 2000, 1840, 1400 | 35D 1760, 1560, 2240 | 37D 2280, 3000, 3600 |
| 29D 1560, 920, 840 | 46D 2120, 1760, 1800 | 43D 2640, 2800, 2920 | 44D 2520, 1880, 2400 |
| 39D 1200, 1520, 1200 | 47D 2620, 2720, 2480 | 45D 1680, 2760, 3160 | 48D 2920, 2440, 2400 |

TABLE I-continued

Group 2 results (Gloved Palmar Skin)

| 0% | 25% | 37% | 50% |
|---|---|---|---|
| 8A 300, 500, 300 | 9A 900, 800, 500 | 4A 800, 1200, 900 | 1A 1840, 2240, 1600 |
| 10A 200, 200, 400 | 14A 300, 800, 800 | 19A 800, 700, 800 | 6A 1100, 1200, 1100 |
| 11A 600, 700, 700 | 15A 700, 700, 900 | 23A 1200, 1300, 1700 | 18A 1500, 1500, 1300 |
| 12A 400, 400, 400 | 44A 800, 800, 1000 | 32A 1000, 1000, 1200 | 26A 1400, 1800, 1300 |
| 27A 300, 700, 800 | 61A 600, 800, 700 | 33A 1200, 2000, 1800 | 34A 1700, 1600, 1000 |
| 31A 400, 600, 800 | 63A 900, 1400, 1200 | 35A 900, 1800, 800 | 48A 1600, 1500, 2000 |
| 37A 400, 700, 600 | 65A 800, 800, 800 | 42A 1600, 1500, 900 | 54A 1400, 2300, 2200 |
| 66A 200, 300, 400 | 69A 1300, 1300, 900 | 45A 800, 800, 1200 | 57A 900, 1300, 1600 |
| 73A 100, 200, 200 | 74A 800, 700, 1100 | 46A 1300, 1800, 1900 | 68A 1800, 1400, 1500 |
| 83A 200, 300, 300 | 97A 500, 500, 500 | 56A 900, 900, 1000 | 75A 1200, 1000, 1200 |
| 85A 500, 400, 400 | 81A 700, 600, 600 | 59A 1000, 900, 1300 | 79A 1100, 1000, 1400 |
| 88A 200, 200, 200 | 91A 500, 600, 600 | 94A 900, 900, 1000 | 80A 1600, 1600, 2000 |

| 62% | 75% | 87% | 100% |
|---|---|---|---|
| 16A 1500, 1300, 1200 | 2A 2900, 2800, 2700 | 5A 3600, 2300, 3600 | 22A 2400, 3000, 2900 |
| 21A 1500, 2200, 2200 | 3A 1600, 4500, 3900 | 13A 2700, 2400, 2300 | 25A 3100, 3600, 2300 |
| 24A 2000, 1700, 1600 | 7A 1800, 2200, 2700 | 17A 2700, 2900, 3300 | 30A 3400, 2800, 5600 |
| 29A 1500, 1900, 1400 | 20A 2200, 3200, 3200 | 28A 4600, 3100, 3000 | 40A 6000, 5100, 4000 |
| 47A 2400, 2300, 3500 | 36A 4800, 4500, 4200 | 39A 3900, 3000, 3200 | 43A 4900, 3200, 3400 |
| 49A 3000, 2600, 2400 | 38A 3200, 3500, 3600 | 41A 3300, 3500, 3400 | 51A 3100, 3000, 2900 |
| 52A 1200, 1100, 2100 | 50A 1900, 2400, 2000 | 64A 3900, 3200, 5500 | 62A 4900, 3100, 2700 |
| 55A 1400, 1200, 1800 | 53A 3100, 2200, 3100 | 76A 2400, 2600, 2800 | 67A 4900, 4500, 2900 |
| 58A 1300, 1900, 2100 | 71A 1400, 2300, 2000 | 84A 3800, 2800, 2700 | 70A 2800, 3300, 3200 |
| 60A 900, 1200, 1000 | 72A 2100, 1800, 2600 | 89A 2200, 2000, 2200 | 87A 4200, 3200, 3000 |
| 82A 1700, 1500, 1800 | 78A 1800, 2000, 2300 | 93A 2300, 3000, 2100 | 90A 2500, 3400, 2700 |
| 96A 2200, 2000, 2900 | 86A 2100, 2200, 3500 | 95A 2400, 2900, 2800 | 92A 2800, 2400, 3300 |

Group 3 Results (Abdominal Rectus Muscle/Fascia vs. Gloved Plantar Skin):

| 0% | 25% | 37% | 50% |
|---|---|---|---|
| 8B 50, 350 | 7B 550, 1200 | 6B 500, 800 | 1B 750, 2600 |
| 9B 50, 400 | 10B 450, 1450 | 12B 350, 1600 | 5B 600, 3050 |
| 19B 50, 300 | 21B 350, 900 | 10B 600, 1350 | 13B 450, 1800 |
| 28B 150, 450 | 37B 700, 1150 | 20B 450, 1200 | 25B 600, 2400 |
| 53B 200, 700 | 38B 450, 1100 | 24B 550, 1350 | 32B 250, 2650 |
| 54B 50, 450 | 51B 250, 1150 | 30B 450, 1250 | 35B 350, 1150 |
| 73B 100, 300 | 56B 300, 150 | 39B 350, 1050 | 40B 1000, 1850 |
| 75B 50, 300 | 60B 500, 1600 | 45B 550, 1400 | 52B 500, 2450 |
| 77B 50, 500 | 65B 550, 1400 | 48B 350, 1300 | 67B 550, 1900 |
| 90B 50, 400 | 83B 350, 1100 | 59B 800, 1750 | 70B 1400, 1750 |
| 89B 100, 550 | 84B 700, 1200 | 68B 700, 1200 | 78B 600, 2250 |
| 91B 50, 250 | 85B 400, 1100 | 92B 400, 1200 | 87B 750, 2300 |

| 62% | 75% | 87% | 100% |
|---|---|---|---|
| 2B 650, 2450 | 4B 350, 3300 | 15B 700, 4850 | 3B 750, 5000+ |
| 11B 500, 2850 | 14B 1500, 3000 | 26B 800, 5000+ | 17B 700, 5000+ |
| 22B 850, 2400 | 18B 1150, 3600 | 29B 300, 4150 | 24B 1800, 5000+ |
| 34B 750, 2750 | 23B 400, 3750 | 31B 900, 5000+ | 42B 300, 5000+ |
| 36B 850, 2500 | 33B 1400, 4250 | 44B 1050, 4900 | 49B 1000, 5000+ |
| 41B 900, 2150 | 43B 950, 3600 | 57B 1350, 5000+ | 62B 1550, 5000+ |
| 46B 600, 3100 | 47B 1100, 4750 | 58B 1300, 5000+ | 64B 750, 5000+ |
| 61B 850, 2500 | 50B 700, 2150 | 69B 1300, 2950 | 74B 1200, 5000+ |
| 67B 1100, 3750 | 55B 900, 4450 | 71B 2550, 4500 | 76B 600, 5000+ |
| 79B 500, 3350 | 66B 900, 4950 | 80B 1350, 5000+ | 82B 1000, 5000+ |
| 81B 700, 3300 | 72B 1900, 4500 | 88B 900, 5000+ | 86B 1550, 5000+ |
| 94B 250, 3000 | 93B 1050, 4650 | 96B 1700, 4450 | 95B 1150, 5000+ |

Group 4 Results (Intercostal Fascia/Muscle:

| 0% | 25% | 37% | 50% |
|---|---|---|---|
| 21C 40, 80, 80 | 9C 720, 480, 200 | 13C 800, 1000, 440 | 8C, 1040, 1440, 520 |
| 24C 40, 40, 80 | 15C 360, 200, 280 | 16C 320, 440, 480 | 14C 720, 480, 600 |
| 36C 160, 200, 120 | 19C 200, 480, 200 | 20C 600, 440, 840 | 22C 400, 400, 760 |
| 41C 80, 80, 80 | 34C 520, 240, 320 | 30C 200, 360, 280 | 27C 400, 320, 720 |
| 43C 80, 80, 40 | 37C 400, 520, 200 | 31C 400, 560, 320 | 29C 520, 480, 400 |
| 48C 40, 80, 40 | 39C 400, 240, 320 | 45C 440, 480, 480 | 42C 360, 440, 480 |

| 62% | 75% | 87% | 100% |
|---|---|---|---|
| 3C 880, 640, 600 | 1C 1060, 880, 960 | 5C 1800, 920, 1160 | 4C 960, 1960, 1320 |
| 10C 480, 480, 880 | 2C 1200, 600, 920 | 7C 1760, 2400, 1080 | 32C 1600, 760, 800 |
| 11C 1200, 880, 1600 | 6C 920, 1200, 1600 | 23C 520, 600, 1200 | 35C 1840, 1800, 1000 |
| 17C 800, 840, 840 | 12C 560, 1560, 760 | 28C 720, 1520, 1520 | 44C 1120, 720, 560 |
| 26C 720, 480, 440 | 18C 520, 960, 560 | 33C 1360, 1000, 840 | 46C 880, 1600, 1000 |
| 40C 400, 440, 720 | 25C 200, 480, 1120 | 38C 1400, 720, 600 | 47C 1720, 1160, 1360 |

Figure 2:
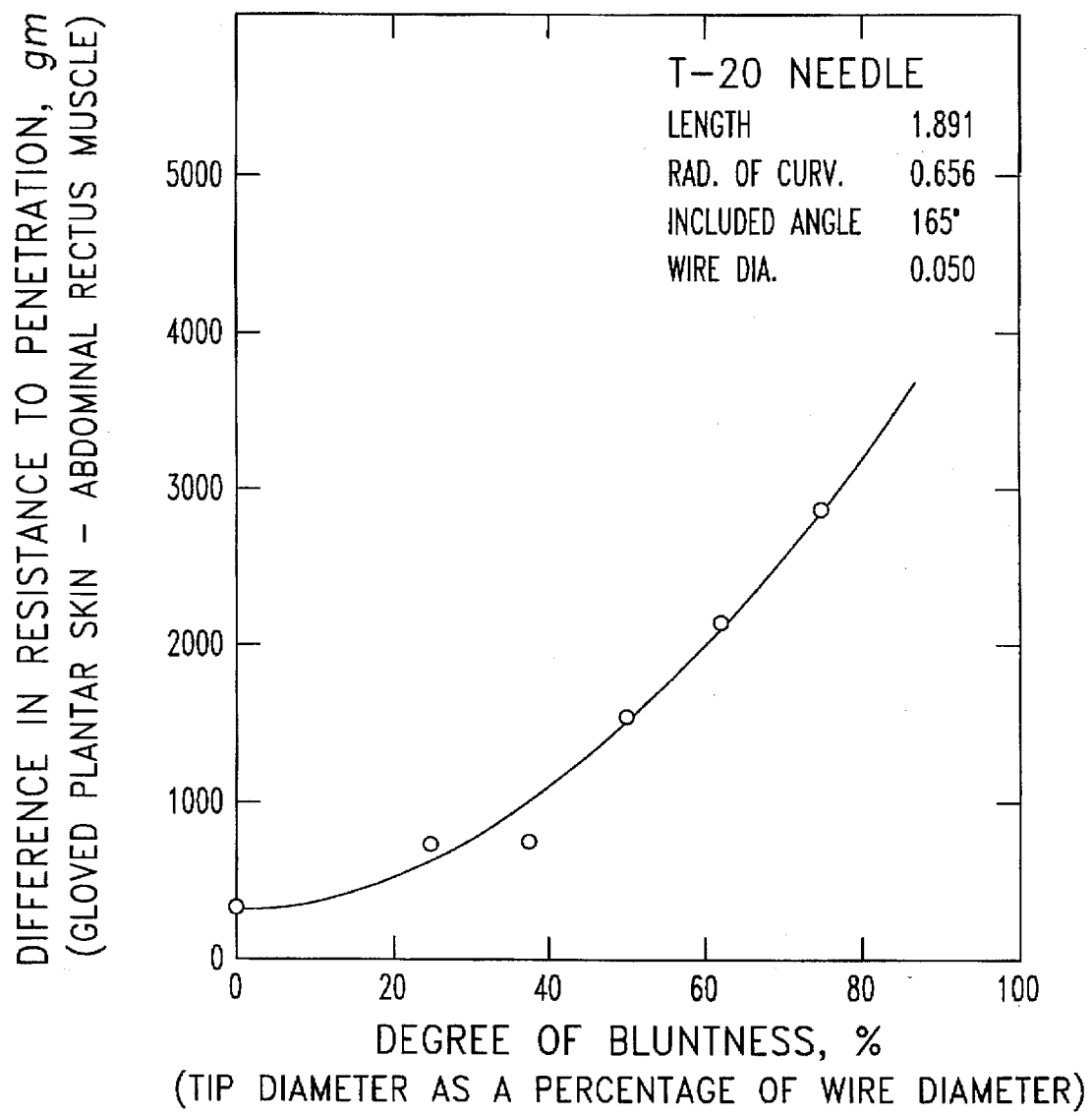
FIG. 2 is a graph showing the variation in difference in resistance to penetration between gloved plantar skin and abdominal rectus muscle as a function of needle bluntness using data obtained from Table III.

The data set forth in Table I is shown in graph form in FIG. 1, wherein resistance to penetration is plotted along the vertical axis and degree of tip bluntness, expressed as a percentage, is plotted along the horizontal axis. Proceeding from uppermost to lowest, the four curves in FIG. 1 correspond to gloved plantar skin, gloved palmar skin, abdominal rectus muscle, and intercostal muscle, respectively. As can be seen with reference to FIG. 1, at all bluntness settings both gloved palmer skin and gloved plantar skin exhibit a greater resistance to penetration than do abdominal rectus fascia/muscle or intercostal fascia/muscle. Further, as can be seen with reference to FIG. 2, the difference in penetration force between gloved skin (plantar) and fascia/muscle (abdominal rectus) remains about the same for needle bluntness in the range between about 0 and 25%. However, as the degree of needle bluntness approaches about 25%, the difference in penetration force between gloved skin (palmar) and fascia/muscle (abdominal rectus) beans to increase. This difference in penetration force continues to increase throughout the remaining range of needle bluntness. It is also perceived from these tests that at bluntness settings greater than about 62% the resistance to penetration of the type needle becomes sufficiently great in abdominal rectus and intercostal fascia/muscle that usage would be disfavored.

Figure 3:
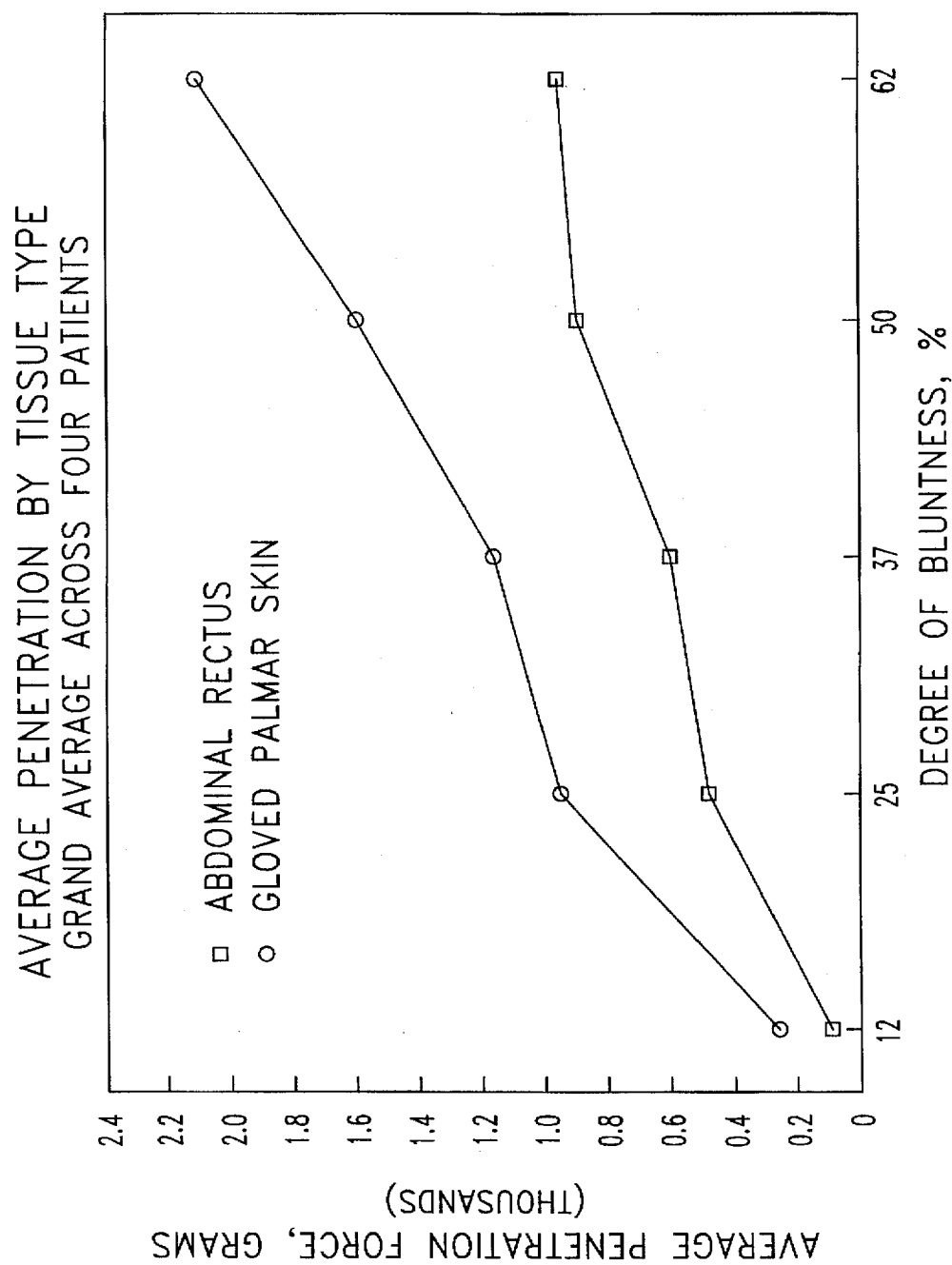
FIG. 3 is a graph showing the variation in average penetration force as a function of needle bluntness using data obtained from Table III.

In a second series of tests, needles having bluntness settings in a range from 25% to 62% were tested in comparison with totally sharp needles having 0% bluntness. The specific bluntness settings tested were 0%, 25%, 37%, 50%, and 62%. Thirty-two penetration measurements were taken at each bluntness setting, broken into four test series identified as A, B, C and D. Each test series was done on a single cadaver. For each test, a needle was passed through muscle fascia and the required penetration force was recorded. Thus, this series of tests involved 160 needles. Table II shows the raw data obtained while Table III presents a statistical summary of the results of these tests. FIG. 3 is a graph showing the variation in average penetration force as a function of needle bluntness using data obtained from Table III. In Table III "Avg" refers to the average force of penetration expressed in grams of the thirty-two tests conducted at each bluntness setting, while "SD" refers to the standard deviation of the test results.

TABLE II

| Cadaver | Bluntness Setting | Abdom Rectus Muscle/Fascia | Gloved Palmar Skin | Difference |
|---|---|---|---|---|
| A | 0% | 80.0 | 340.0 | 260.0 |
| B | 0% | 80.0 | 225.0 | 145.0 |
| C | 0% | 145.0 | 285.0 | 140.0 |
| D | 0% | 65.0 | 210.0 | 145.0 |
| A | 25% | 345.0 | 835.0 | 490.0 |
| B | 25% | 375.0 | 845.0 | 470.0 |
| C | 25% | 860.0 | 1355.0 | 495.0 |
| D | 25% | 350.0 | 775.0 | 425.0 |
| A | 37% | 515.0 | 925.0 | 410.0 |
| B | 37% | 400.0 | 1000.0 | 600.0 |
| C | 37% | 1040.0 | 1660.0 | 620.0 |
| D | 37% | 465.0 | 1080.0 | 615.0 |
| A | 50% | 910.0 | 1480.0 | 570.0 |
| B | 50% | 555.0 | 1370.0 | 815.0 |
| C | 50% | 1450.0 | 2400.0 | 950.0 |
| D | 50% | 665.0 | 1145.0 | 480.0 |
| A | 62% | 595.0 | 1420.0 | 825.0 |
| B | 62% | 695.0 | 1610.0 | 915.0 |
| C | 62% | 1755.0 | 3495.0 | 1740.0 |
| D | 62% | 775.0 | 1930.0 | 1155.0 |

TABLE III

| Bluntness Setting | Muscle/Fascia | Gloved Skin | Difference |
|---|---|---|---|
| 0% | Avg = 92.5<br>SD = 41.2 | Avg = 265.0<br>SD = 70.9 | Avg = 172.5<br>SD = 69.2 |
| 25% | Avg = 482.5<br>SD = 298.6 | Avg = 952.5<br>SD = 350.8 | Avg = 470.0<br>SD = 274.1 |
| 37% | Avg = 605.0<br>SD = 325.6 | Avg = 1166.3<br>SD = 399.2 | Avg = 561.3<br>SD = 350.8 |
| 50% | Avg = 895.0<br>SD = 492.7 | Avg = 1598.8<br>SD = 605.7 | Avg = 703.8<br>SD = 445.6 |
| 62% | Avg = 955.0<br>SD = 538.5 | Avg = 2113.8<br>SD = 969.4 | Avg = 1158.8<br>SD = 619.6 |

It is perceived that the degree of safety provided to an operator by a particular needle configuration is directly related to the magnitude of difference in the penetration force needed to pierce the target body tissues and the gloved hand of the operator. As is indicated by the data in Table III, a totally sharp needle having 0% bluntness requires an average of 172.5 grams greater penetration force to penetrate gloved skin as compared to muscle fascia. This "safety factor" of 172.5 grams is of course insufficient in many instances in preventing accidental sticks of the gloved hand of the operator. The Table III results show that needles having a bluntness in the 25–62% range exhibit a much greater magnitude of difference in the penetration force needed to pierce the target body tissues and the gloved hand of the operator than sharp needles (i.e., needles having 0% bluntness).

Table IV indicates the average percent improvement in the safety factor provided by 25–62% blunt needles over sharp (0% blunt) needles, based on the Tables II and III data. The average percent improvement in the safety factor is defined by the following formula wherein $A_{sf}$ is the average percent improvement in the safety factor, $P_b$ is the average gloved skin penetration force at bluntness setting b, and $P_o$ is the average gloved skin penetration force for a sharp (0% blunt) needle:

$$A_{sf}=(P_b/P_o)\times 100$$

TABLE IV

| Bluntness Setting | $P_o$ | $P_b$ | Improvement |
|---|---|---|---|
| 25% | 265.0 | 952.5 | 359.4% |
| 37% | 265.0 | 1166.3 | 440.1% |
| 50% | 265.0 | 1598.8 | 603.3% |
| 62% | 265.0 | 2113.8 | 797.6% |

Table V shows the minimum percent improvement in safety, defined by the following formula:

$$M_{sf}=(P_b*/P_o)\times 100$$

In the above formula, $M_{sf}$ is the minimum percent improvement in the safety factor. $P_b*$ is the minimum gloved skin penetration force at bluntness setting b calculated by subtracting the standard deviation in penetration force at bluntness setting b from the average penetration force at bluntness setting b. Thus, 84% of the penetrations at bluntness setting b will be higher than $P_b*\cdot P_o$ is the average gloved skin penetration force for a sharp (0% blunt) needle.

TABLE V

| Bluntness Setting | $P_o$ | $P_b$* | Improvement |
|---|---|---|---|
| 25% | 265.0 | 601.7 | 227.1% |
| 37% | 265.0 | 767.1 | 289.5% |
| 50% | 265.0 | 993.1 | 374.8% |
| 62% | 265.0 | 1144.4 | 431.8% |

Figure 4:
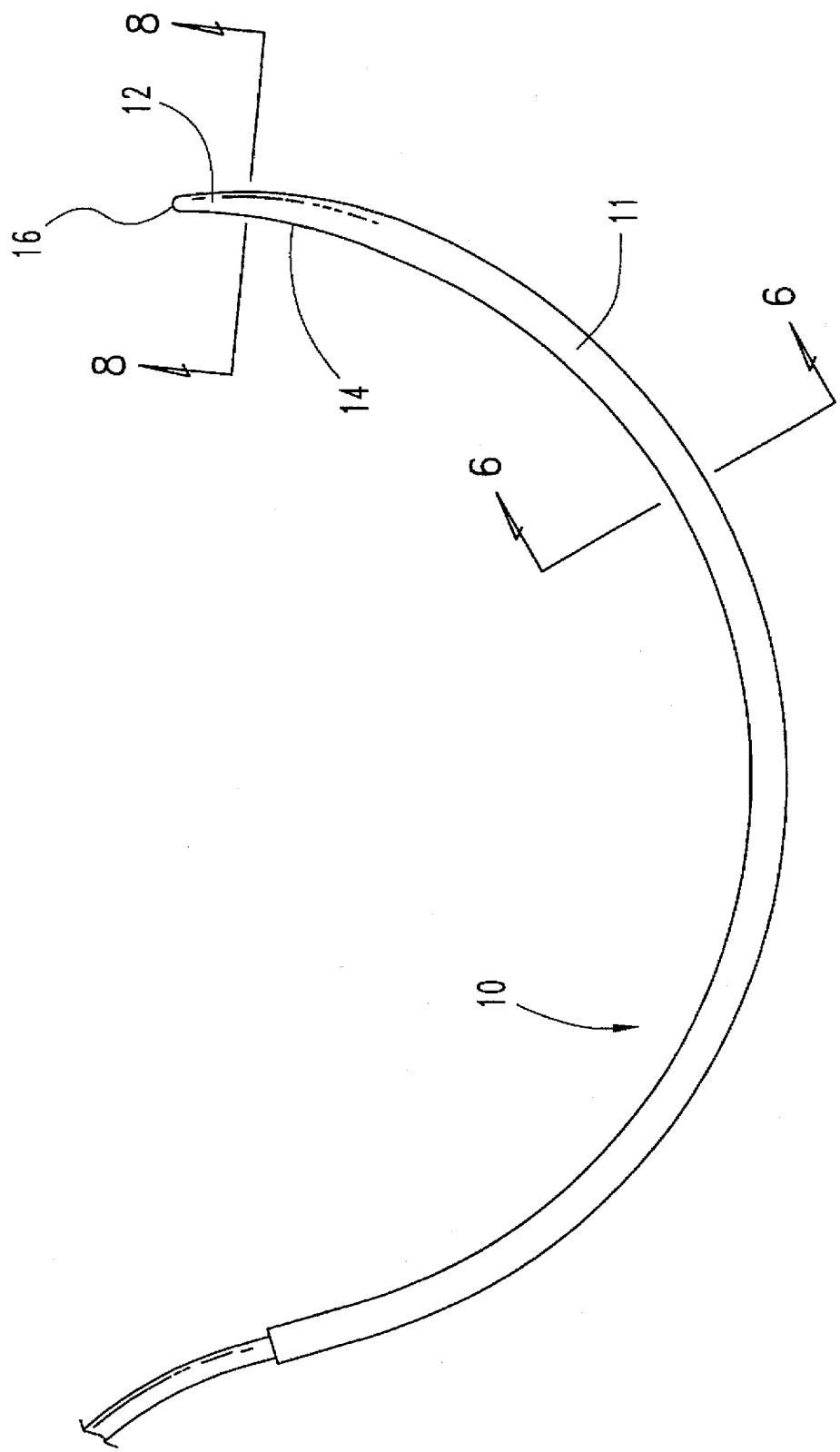
FIG. 4 is a side view of a preferred embodiment of the surgical needle of the present invention.
Figure 5:
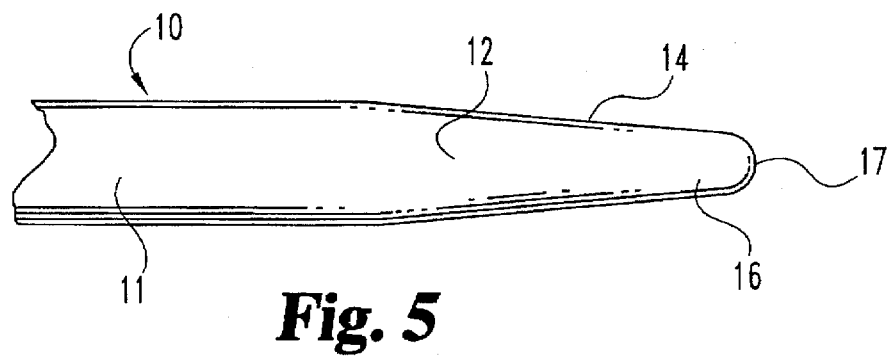
FIG. 5 is an enlarged fragmentary view of the tip portion of the surgical needle of FIG. 4.
Figure 6:
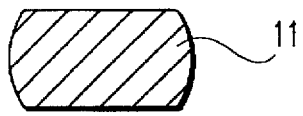
FIG. 6 is an enlarged cross-sectional view taken along lines 6—6 in FIG. 4.
Figure 7:
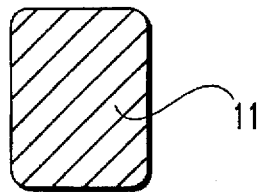
FIG. 7 is an alternative embodiment of the enlarged cross-sectional view taken along lines 6—6 in FIG. 4.
Figure 8:
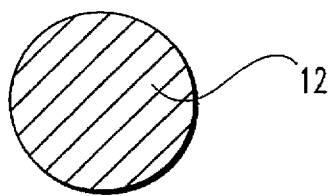
FIG. 8 is an enlarged cross-sectional view taken along lines 8—8 in FIG. 4.

A preferred embodiment of the surgical suture needle of the present invention, incorporating the desired safety characteristics is generally indicated at 10 in FIGS. 4 and 5. The needle 10 has a shaft portion 11 having a uniform outer diameter, and a tip portion 12 integrally formed with shaft portion 11 and extending distally there from. In order to provide stability and control of the needle 10 during use, the shaft portion 11 may have a flat pressed circular cross section such as shown in FIG. 6 or, alternatively, a modified square cross sectional shape such as shown in FIG. 7. In the needle 10 of FIG. 4 the shaft portion 11 is curved and possesses a constant radius of curvature. This configuration is, however, not critical to the present invention and shaft portion 11 may therefore assume any straight and/or curved configuration which is considered suitable for the particular purpose that is intended. Both the shaft portion 11 and tip portion 12 are rigidly formed of a suitable material for suture needle use inside the body, such as surgical grade steel. The needle tip portion 12 has an essentially circular cross sectional shape, as shown in FIG. 8, and a tapered body 14. The needle tip portion 12 terminates in a blunt head 16 which is configured to permit piercing of muscle and fascia, muscle alone, adipose, pericostal tissue and other non-cutaneous soft tissues of the body While preventing skin penetration of the gloved hand of an operator. As can be best appreciated with reference to FIG. 5, head 16 preferably has a part spherical shape which encompasses vertex 17 of tip portion 12. Other curved shapes may also be employed as suitable configurations for head 16, so long as there are no sharp edge surfaces.

It should be noted that the surgical needle of the present invention is specifically designed such that it is not suitable for suturing cutaneous tissues. Accordingly, based upon the test results obtained, it is considered important that blunt head 16 have a minimum diameter of curvature which is at least 25% of the diameter of the needle shaft portion 11 and a maximum diameter of curvature which no greater than about 62% of the diameter of the needle shaft. Within this range, it is perceived that needles having a bluntness which is toward the higher end of the range will be especially preferred as they offer a greater safety factor while still being acceptable for use. Further, the diameter of the needle shaft should be in a range of about 0.026" to 0.050" with the diameter of curvature of the needle tip ranging between about 0.006" to about 0.031". In addition, it is considered critical that the entire needle tip portion has a continuously smooth outer surface lacking any discontinuities or sharp cutting edges.

In practice, the surgical suture needle of the present invention may be used to close non-cutaneous soft tissues of the body employing the same techniques used with conventional suture needles. However, since the cutaneous tissues of the wound cannot be closed with the blunt tip needle, another closing technique must be used to complete the wound closure. This does not pose a problem, however, in that it is quite common to employ different closing techniques for closing the cutaneous and non-cutaneous tissues in a wound. For example, the needle of the present invention may be used to close the non-cutaneous tissues while final closure of the cutaneous tissues may be accomplished by conventional stapling techniques.

It is perceived that the blunt needle off the present invention may, in addition to reducing the risk of infectious disease transmission by reducing the risk of an accidental needle stick, also serve to reduce the risk of needle contamination by reducing the amount of bleeding caused by the needle. Decreased bleeding occurs because the blunt needle is more likely to simply push blood vessels aside rather than penetrate them as it is being advanced in the body.

While the invention has been illustrated and described in detail in the drawings and foregoing description, the same is to be considered as illustrative and not restrictive in character, it being understood that only the preferred embodiment has been shown and described and that all changes and modifications that come within the spirit or the invention are desired to be protected.

What is claimed is:

1. A surgical suture needle for use in directly piercing non-cutaneous soft tissues of the body, comprising:
   a needle shaft; and
   a needle tip, said needle shaft and needle tip having a solid interior lacking any lumen communicating with the exterior of said needle and formed of a rigid material suitable for use inside the body, said needle tip having a body portion integrally formed with and extending from said needle shaft, said body portion being tapered along the length thereof, said needle tip further having a blunt head adapted to penetrate muscle and fascia, muscle alone, adipose, pericostal tissue and other non-cutaneous soft tissues of the body while preventing skin penetration of the gloved hand of an operator and wherein said needle has a continuously smooth outer surface lacking any sharp cutting edges.

2. The surgical needle of claim 1 wherein said blunt head has a part spherical shape and a vertex which forms a portion of said part spherical shape.

3. The surgical needle of claim 2 wherein said blunt head has a diameter of curvature which is at least 25% of the diameter of said needle shaft and said diameter of curvature is at least about 0.006".

4. The surgical needle of claim 3 wherein said blunt head having a diameter of curvature in the range of 25% to 62% of the diameter of said needle shaft.

5. The surgical needle of claim 3 wherein said diameter of curvature of said needle tip is no greater than about 0.031".

6. The surgical needle of claim 1 wherein said needle shaft has a generally flat pressed circular cross-section in order to facilitate stability in a needle holder.

7. The surgical needle of claim 1 wherein said needle tip has a generally circular cross-section.

8. The surgical needle of claim 1 wherein the diameter of said needle shaft is in a range of about 0.026" to 0.050".

9. A surgical suture needle for use in directly piercing muscle and fascia, muscle alone, adipose, pericostal tissue and other non-cutaneous soft tissues of the body, comprising:
   a needle shaft portion having a generally circular cross-section; and
   a needle tip portion having a generally circular cross-section, said needle tip portion further having a body segment and a blunt head, said body segment being tapered along the length thereof, said blunt head having a part spherical shape and a vertex which forms a portion of said part spherical shape, said blunt head having a diameter of curvature which is at least 25% of the diameter of said needle shaft to thereby prevent skin penetration of the gloved hand of an operator, and wherein said needle tip portion and needle shaft portion have a solid interior lacking any lumen communicating with the exterior of said needle.

10. The surgical needle of claim 9 wherein said diameter of curvature is in a range of 25% to 62% of the diameter of said needle shaft.

11. The surgical needle of claim 10 wherein the diameter of said needle shaft is in a range of about 0.026" to 0.050".

12. The surgical needle of claim 10 wherein said diameter of curvature of said needle tip is in a range between about 0.006" to about 0.031".

13. A taper point surgical suture needle for use in directly piercing non-cutaneous soft tissues of the body, comprising:

a needle shaft; and a means, located at the tip of said needle and extending integrally from said needle shaft, for penetrating muscle and fascia, muscle alone, adipose, pericostal tissue and other non-cutaneous soft tissues of the body while preventing skin penetration of the gloved hand of an operator, said needle shaft and tip means being formed of a rigid material suitable for use inside the body, said tip means having a tapered body portion integrally formed with and extending from said needle shaft, said tip means further including a blunt head integrally formed with and extending from said body portion, said tip means having a continuously smooth outer surface lacking any sharp cutting edges, and said tip means and needle shaft have a solid interior lacking any lumen communicating with the exterior of said needle.

14. The surgical needle of claim 13 wherein said blunt head has a part spherical shape and a vertex which forms a portion of said part spherical shape, said blunt head having a diameter of curvature which in a range from about 50% to 62% of the diameter of said needle shaft.

15. A surgical suture needle for use in directly piercing non-cutaneous soft tissues of the body, comprising:

a needle shaft; and a needle tip, said needle shaft and needle tip formed of a rigid material suitable for use inside the body, said needle tip having a body portion integrally formed with and extending from said needle shaft, said body portion being tapered along the length thereof, said needle tip further having a blunt head adapted to penetrate muscle and fascia, muscle alone, adipose, pericostal tissue and other non-cutaneous soft tissues of the body while preventing skin penetration of the gloved hand of an operator, said blunt head having a part spherical shape and a vertex which forms a portion of said part spherical shape, said blunt head being formed so as to provide a safety factor of at least 200% over a needle having 0% bluntness, and wherein said needle tip and needle shaft have a solid interior lacking any lumen communicating with the exterior of said needle.

16. The surgical needle of claim 15 wherein said blunt head is formed so as to provide a safety factor of between about 200% to 800% over a needle having 0% bluntness.

* * * * *